| United States Patent [19] | [11] 4,107,442 |
|---|---|
| Quinn | [45] Aug. 15, 1978 |

[54] PROCESS FOR PREPARING DIHYDROXYDIPHENYL CHLOROETHYLENES

[75] Inventor: Clayton B. Quinn, Mt. Vernon, Ind.

[73] Assignee: General Electric Company, Schenectady, N.Y.

[21] Appl. No.: 825,574

[22] Filed: Aug. 18, 1977

Related U.S. Application Data

[63] Continuation-in-part of Ser. No. 789,019, Apr. 20, 1977, abandoned.

[51] Int. Cl.² .................................. C07C 37/00
[52] U.S. Cl. ........................... 568/726; 260/613 R
[58] Field of Search ........................... 260/619 A

[56] References Cited

U.S. PATENT DOCUMENTS 4,073,814  2/1978  Kinson et al. .................. 260/619 A

*Primary Examiner*—Norman Morgenstern
*Attorney, Agent, or Firm*—Joseph T. Cohen; Charles T. Watts; Marvin Snyder

[57] ABSTRACT

The compound 1,1-dichloro-2,2-bis-(4-hydroxyphenyl) ethylene can be prepared by the reaction of 1,1-dichloro-2,2-diphenoxy ethylene and phenol in the presence of $BF_3$ gas and methylene chloride. The formed dihydroxydiphenyl chloroethylene can be treated with a phosgenating agent to form polycarbonate resins which can be used in applications where flame retardancy is desired.

1 Claim, No Drawings

PROCESS FOR PREPARING DIHYDROXYDIPHENYL CHLOROETHYLENES

This application is a continuation-in-part of my earlier application Ser. No. 789,019, filed Apr. 20, 1977 now abandoned and assigned to the same assignee as the present invention.

This invention is concerned with making dihydroxydiphenyl chloroethylenes. More particularly, the invention relates to the preparation of the compound 1,1-dichloro-2,2-bis-(4-hydroxyphenyl)ethylene having the formula

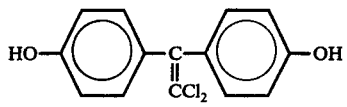

I by effecting reaction between 1,1-dichloro-2,2-diphenoxy dichloroethylene of the formula

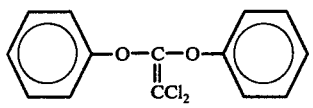

II with phenol in the presence of $BF_3$ gas and methylene chloride. The dihydroxydiphenyl compound of formula I can be treated with a phosgenating agent such as phosgene or diphenyl carbonate to make polycarbonate resins (as described in Polish Pat. No. 48,893 issued Dec. 12, 1964) which have good impact characteristics and flame-retardant properties. These properties recommend that such polymers be used in various molding and coating applications such as housings for electric equipment, grills for automobiles, etc.

The diphenyl dichloroethylene compound of formula II is described and can be prepared in the manner described in my copending application Ser. No. 789,020 filed Apr. 20, 1977, and assigned to the same assignee as the present invention. By reference this application is intended to be included within the disclosures and teachings of the instant application.

The reaction between the phenol and the disphenyl dischloroethylene compound of formula II is advantageously carried out under atmospheric pressures (although superpressures are not precluded) employing at least 2 mols of the phenol per mol of the diphenyl dichloroethylene compound. Excess molar quantities of the phenol up to 3 to 5 or more mols may be used without departing from the scope of the invention.

The temperature of the reaction is not critical and can be varied widely; thus, temperatures of from about 20° to 100° C. can be advantageously employed. Usually room temperature reactions are adequate for the purpose since the reaction is exothermic and often requires cooling in order to avoid excessive heating of the reaction. The time of reaction can also be varied widely, ranging from about 1 hour to 36 hours or more depending on the temperature at which the reaction is carried out.

The amount of $BF_3$ used can be quite small and may range on a weight basis from about 0.001 to 0.1 part of the acidic composition per part of the total weight of the phenol and the diphenyl dichloroethylene compound.

Inert solvents are advantageously employed in the practice of the invention. A particularly effective inert solvent is methylene chloride which can be employed, by weight, from 1 to 100 parts of the latter per part of the total weight of the phenol and the compound of formula II. An inert atmosphere, such as a nitrogen atmosphere, is helpful in order to minimize any side reactions.

In order that those skilled in the art may better understand how the present invention may be practiced, the following examples are given by way of illustration and not by way of limitation.

The diphenyl dichloroethylene compound used in the following example was prepared as follows:

To a reaction vessel were added 25 grams tetrachloroethylene, 365 ml dimethyl sulfoxide, 28.3 grams phenol and 19.83 grams potassium hydroxide. While passing nitrogen over the reaction mixture, the mixture was heated at about 135° to 140° C. for 12 hours. At the end of this time, the reaction mixture was allowed to cool, diluted with about an equal volume of water and the aqueous solution extracted three times with 200 ml diethyl ether. The combined extracts were washed three times with water, dried over magnesium sulfate, the ether evaporated, and the residue distilled to give a 50% yield of the diphenyl dichloro compound of formula II.

EXAMPLE 1

A mixture was made of 1.0 gram of the diphenoxy dichloroethylene of formula II, and 1.7 grams phenol and 10 ml methylene chloride. Thereafter, under a nitrogen atmosphere and at room temperature, the mixture was treated with $BF_3$ gas until 150 mg had been adsorbed. Analysis of the mixture showed a 15% yield of the compound of formula I. When the methylene chloride was omitted or $BF_3$ etherate with methylene chloride was used, only trace amounts of the compound of formula I could be detected.

It will of course be apparent to those skilled in the art that in addition to the conditions under which the foregoing examples were carried out, other conditions of reaction can be employed in accordance with the above description. Moreover, within the scope of the intended invention, the amount and ratio of ingredients can also be varied.

What I claim as new and desire to secure by Letters Patent is:

1. The process for preparing the dihydroxydiphenyl compound, 1,1-dichloro-2,2-bis-(4-hydroxyphenyl)ethylene having the formula

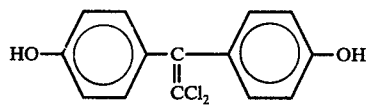

which comprises effecting reaction between 1,1-dichloro-2,2-diphenoxy ethylene with phenol in the presence of $BF_3$ gas and methylene chloride, and thereafter isolating the aforementioned dihydroxydiphenyl compound.

* * * * *